United States Patent [19]

Tyson

[11] Patent Number: 4,842,877

[45] Date of Patent: Jun. 27, 1989

[54] DELIGNIFICATION OF NON-WOODY BIOMASS

[75] Inventor: George J. Tyson, Madison, Wis.

[73] Assignee: Xylan, Inc., Madison, Wis.

[21] Appl. No.: 177,786

[22] Filed: Apr. 5, 1988

[51] Int. Cl.$^4$ .............................................. A23K 1/00
[52] U.S. Cl. .................................... 426/271; 426/443; 426/615; 426/804; 426/807; 127/37
[58] Field of Search ................... 426/271, 615, 804, 2, 426/807, 623, 630, 636, 443; 127/1, 37

[56] References Cited

U.S. PATENT DOCUMENTS

| | | |
|---|---|---|
| 3,069,309 | 12/1962 | Fennell . |
| 4,136,207 | 1/1979 | Bender . |
| 4,187,141 | 2/1980 | Ahrel . |
| 4,214,947 | 7/1980 | Berger . |
| 4,241,093 | 12/1980 | Farag et al. ........................ 426/259 |
| 4,298,425 | 11/1981 | Ranzen et al. . |
| 4,311,553 | 1/1982 | Akerlund et al. . |
| 4,316,747 | 2/1982 | Rugg et al. ............................ 127/1 |
| 4,316,748 | 2/1982 | Rugg et al. ............................ 127/1 |
| 4,372,812 | 2/1983 | Phillips et al. . |
| 4,390,375 | 6/1983 | Rugg et al. ............................ 127/1 |
| 4,444,621 | 4/1984 | Lindahl . |
| 4,451,332 | 5/1984 | Annergren et al. . |
| 4,459,174 | 7/1984 | Papageorges et al. . |
| 4,462,864 | 7/1984 | Carles et al. . |
| 4,478,644 | 10/1984 | Berger et al. ........................... 127/1 |
| 4,568,420 | 2/1986 | Nonni . |
| 4,649,113 | 3/1987 | Gould .................................... 426/2 |
| 4,661,205 | 4/1987 | Ow et al. . |
| 4,728,367 | 3/1988 | Huber et al. ............................ 127/1 |

OTHER PUBLICATIONS

Wenger advertisement, X-200 Continuous Extrusion Cooker, Bulletin No. 31-3R84, 4 pages.

Chementator article from *Chemical Engineering*, Mar. 14, 1988, p. 19.

"There's New Life in Continuous Fermentation", *Chemical Week*, Feb. 22, 1984.

Gould, J. Michael and S. N. Freer, High-Efficiency Ethanol Production from Lignocellulosic Residues Pretreated with Alkaline $H_2O_2$, *Biotech. and Bioengineering*, vol. XXVI, pp. 628-631 (1984).

Easterbrook, Gregg, "A Feeding Machine", *Science*, Jan./Feb. 1986, pp. 48-54.

Potter, Anne Murielle, "Steak or Stake?", *Bio-Joule*, Sep. 1987, pp. 8-9.

*Primary Examiner*—R. B. Penland
*Attorney, Agent, or Firm*—Lathrop & Clark

[57] ABSTRACT

A non-woody biomass is delignified through extrusion technology, utilizing hydrogen peroxide and an alkali agent, to break down complex biomass materials. The process is useful in forming a highly absorbent fiber material for use as a dietary fiber or an absorbent fiber. Alternatively, the process is useful for preparing dietary feeds for ruminant animals, as well as produce a broad range of alcohols or polymers from the non-woody lignocellulosic substrate.

34 Claims, 1 Drawing Sheet

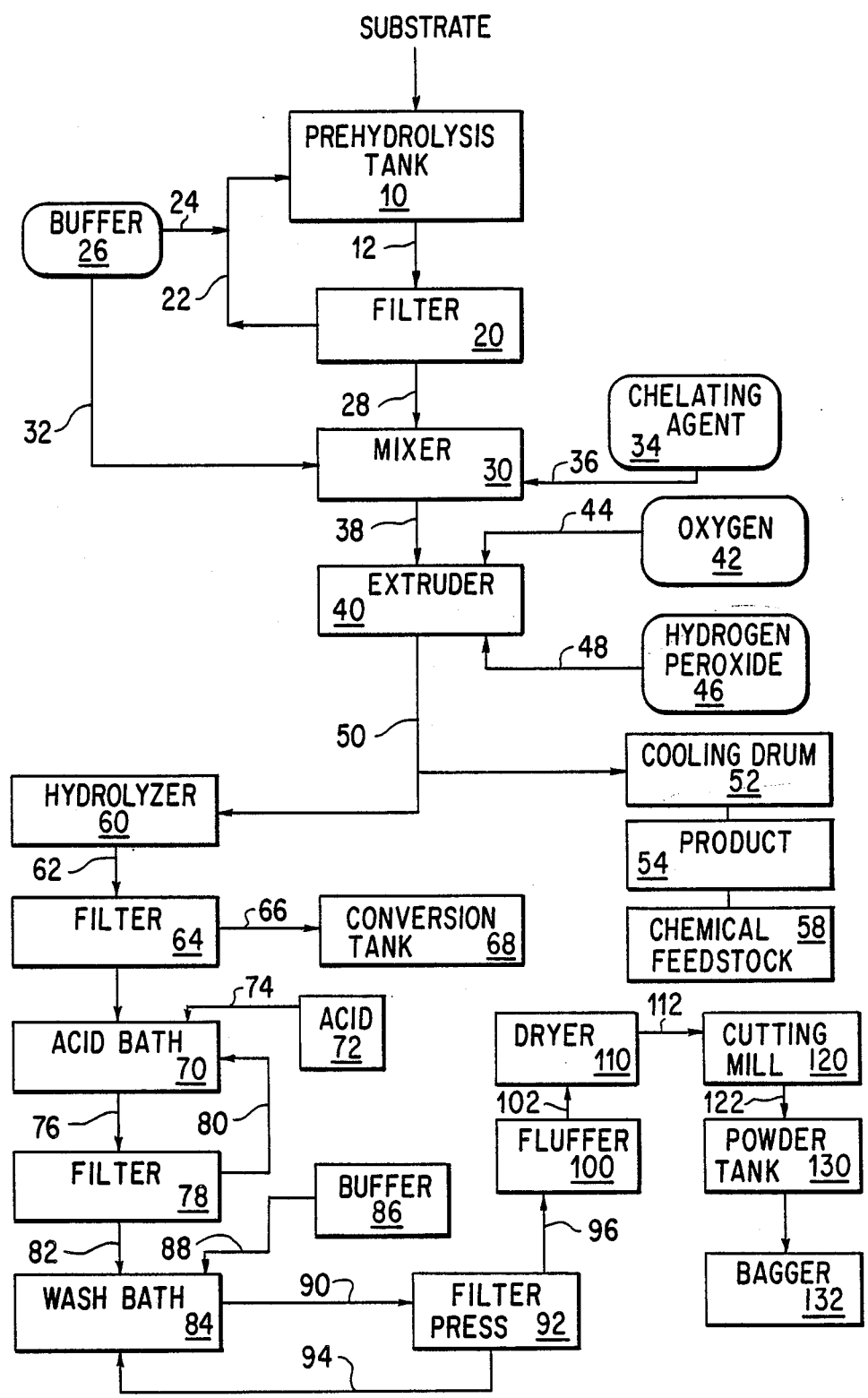

DELIGNIFICATION OF NON-WOODY BIOMASS

FIELD OF THE INVENTION

The present invention is directed to a process and apparatus for the delignification of non-woody biomass through extrusion technology to break down complex biomass materials. Specifically, the present invention is directed to the delignification of non-woody agricultural biomass wastes through extrusion technology, utilizing hydrogen peroxide and an alkali. The invention is particularly directed to the formation of specific chemicals and dietary fiber for use in food products. The present invention is also directed to a process and apparatus for preparing useful dietary feeds for ruminant animals.

BACKGROUND OF THE INVENTION

Description of the Prior Art

The importance of dietary fiber for use in the human and non-human system cannot be overemphasized. Dietary fiber plays a major role in health and disease resistance, physiological metabolism, and in preventive medicine. There has been considerable effort in the development of fiber-containing foods in order to benefit from the advantages of dietary fiber in the system. Further, many of these materials can be used as an effective carbohydrate and energy source in ruminant feeds. However, in order to benefit from these advantages, the lignocellulosic materials in the residues must be converted into materials which can be metabolized by the animal. Specifically, the polysaccharide portion of these agricultural residues have to be converted into monomeric sugars.

In order to accomplish this, it is important to break down the lignin in the residues to release the beneficial polysaccharides in the plant cell wall.

Originally, the delignification process used sulfuric acid and chlorine as the main agents. However, due to environmental control process problems, sulfuric acid is now being replaced with sodium hydroxide and oxygen.

As an example in woody fibers, U.S. Pat. No. 4,459,174 to Papageorges, et al. discloses a process for the delignification and bleaching of chemical and semichemical cellulosic pulps in which the pulp is subjected to a treatment with oxygen and subsequent treatment with peroxide. The effluent from the treatment with peroxide is at least partially recycled to the treatment with oxygen.

U.S. Pat. No. 4,451,332 to Annergren, et al. is directed to a method for the delignification of lignocellulose containing fiber material comprising mixing an oxygen-containing gas with the cellulose fiber material in order to atomize the gas and form a foam of the gas and the cellulose fiber material. This process provides a bleached, delignified cellulose fiber without bleaching the lignin substance extracted from the material.

U.S. Pat. No. 4,372,812 to Phillips, et al. is directed to a chlorine-free bleaching process for lignocellulosic pulp. This process is characterized by a series of bleaching stages comprising in sequence a peroxide bleaching stage, and at least one ozone bleaching stage.

U.S. Pat. No. 4,311,553 to Akerlund, et al. is directed to a method of producing peroxide bleached pulp by impregnating lignocellulose fiber material with an aqueous silicate solution containing a sequestering agent. The fiber material is preheated with saturated steam and defibrated between two grinding disks in an atmosphere of saturated steam at a temperature of 100°–170° C.

U.S. Pat. No. 4,298,425 to Ranzen, et al. is directed to a method and apparatus for producing fiber pulp of improved paper-forming characteristics from lignocellulose-containing material such as wood chips and the like.

U.S. Pat. No. 4,214,947 to Berger is directed to the treatment of a cellulosic material in the form of wood chips to produce at least partial delignification without mechanical grinding. The material is brought into contact with a reagent, e.g., steam or a chemical reagent, and is subjected to alternate increases and decreases in pressure.

U.S. Pat. No. 4,187,141 to Ahrel is directed to a method of producing mechanical pulp of improved brightness and light-scattering properties from wood chips, which are ground between a pair of disks. The chips are impregnated with a solution of alkali and introduced into a pressure vessel which is in communication with the grinding zone.

U.S. Pat. 4,444,621 to Lindahl is directed to a process and apparatus for the deresination and brightness improvement of cellulose pulp, by adding an alkali to the pulp, along with a sufficient oxidizing bleaching agent.

While the above processes are mainly directed to the delignification of woody-like materials, there are other processes known to the art which disclose the delignification of non-woody biomasses to produce food fit for human and animal consumption. For example, U.S. Pat. 4,136,207 to Bender discloses a process for the delignification and fractionation of non-woody substrates using a reactor and acid hydrolysis. This process uses a pH of 1.5 as the first step with heat and pressure and a residence time of 6–13 minutes. Hemicellulose is extracted from the residues, and the residues are subjected to hydrolysis for further fermentation to ethanol, butanol, acetic acid, furfural, and xylitol. The cellulose and lignin are then treated with an alkaline solution and separated for independent uses.

U.S. Pat. No. 4,649,113 to Gould discloses a batch process for the delignification of agricultural residues to produce cattle feeds, chemical feeds or dietary fibers through the separation of these components. The agricultural crop residues and other non-woody lignocellulosic plant substrates are treated with hydrogen peroxide at a controlled pH within the range of about 11.2 to 11.8. The substrates are partially delignified. This process does not use a reactor or mechanical shear and compression device, but utilizes pHs within the range of about 11.2 to 11.8 with hydrogen peroxide in the liquid. The cell walls are fractured in approximately 4 to 6 hours. The product can be used for animal feeds. It is also possible to separate the liquid from the cell walls if dietary fiber as a product is desired.

While there are processes and apparatuses available which delignify both woody and non-woody cellulosic materials, these processes have inherent deficiencies. For example, with the process as disclosed in the '113 patent to Gould, maximum delignification of biomass or non-woody lignocellulosic materials is achieved by the use of substantial amounts of hydrogen peroxide in an aqueous solution at a pH of about 11.5 in stored tanks for 4 to 6 hours at temperatures between approximately 50° and 120° F. With this process, a substantial amount of chemicals must be utilized in order to effect the required delignification of the fiber.

SUMMARY OF THE INVENTION

In accordance with this invention, it is an object to provide a delignification process which permits the efficient utilization of non-woody agricultural residues.

It is also an object of the present invention to provide a process for the delignification of waste or very low value agricultural biomass or industrial waste to produce value-added foods, solvents, or polymers.

It is also an object of the present invention to provide a nontoxic nutritional ruminant feed source at a cost less than traditional energy foods.

It is also an object of the present invention to develop a process which may produce a broad range of alcohols or polymers, such as ethanol, butanol, butanediol, 2-3-L glycerol, acetic acid, furfural, xylitol or single cell proteins.

It is also an object of the present invention to provide grain and seed processors with a new use for their non-woody agricultural residue waste hulls, shells or other waste portions of their processing systems.

It is also an object of the present invention to produce a non-toxic material which produces at least 80% cellulose in a food grade dietary fiber that will be FDA approved.

These and other objects are met by the present invention which discloses a method for continuously treating a non-woody lignocellulosic substrate comprising reacting the substrate in a reaction medium containing an aqueous solution of a strong alkali at a pH in the range of about 10.5 and 12.5. This is followed by adding a chelating agent to the substrate in an amount effective to chelate the metal ions in the substrate. The substrate is then continuously fed into a pressurized extruder reactor conducted in an oxygen atmosphere at a temperature between about 150° and 315° F. and at a pressure between about 250 and 450 psi. The reactor is operated in the presence of hydrogen peroxide, which is added to the extruder at a rate of between about 20 to 40 pounds of hydrogen peroxide per ton of substrate on a dry matter basis.

The process provides a mechanical extrusion system to mix, grind and sterilize non-woody agricultural substrates while mixing them with sodium hydroxide, potassium hydroxide or other buffering agents in the presence of heat, pressure, and hydrogen peroxide. Following the extruder reaction process, the substrate can be passed to a cooling drum for bagging or truck loading, or passed into enzyme and fermentation tanks for production of ethanol, acetic acid or fermentation to 2, 3-butanediol or glycerol, or the substrate can be further processed to produce a high quality dietary fiber.

The process allows the mixture of grains, vegetables and fruits or portions of these plants to be processed together, as well as separately to achieve the proper proportions of non-digestible or soluble dietary fiber.

Without wishing to be limited to one explanation, it is believed that the process of the present invention disrupts the lignin and cellulose comprising the essential part of the cell walls of the plants allowing oxygen to escape. This happens as the bonds between the hydrogen and oxygen erupt. The water and oxygen leave in the form of steam. Hydrogen oxidizes and is eliminated as the pressure is released and as the water hydrolizes hemicellulose, or other polysaccharides, and lignin into the desired proportions to customize the fiber, based on its usage. The biomass may be treated with less hydrogen peroxide and correspondingly less alkali buffering agents, such as sodium hydroxide or potassium hydroxide in order to maintain an adjusted pH of approximately 11.5 and to eliminate the need to handle and dispose of the liquid waste stream.

The dietary food fiber may be produced from any of a number of non-woody biomass sources by use of an extruder, by injecting chemicals into the barrel, at specific points, to custom produce a substrate which can then hydralyzed and/or bleached and separated into the ratios desired to meet the exacting specifications of the baking and food preparation industry.

By the use of non-corrosive extruders, the substrates can be ground and mixed utilizing less chemicals than the prior inventions. For example, the process of the present invention is advantageous over the '113 patent to Gould in that instead of 200 pounds of hydrogen peroxide per ton of dry biomass, the process of the present invention only requires between 20 and 40 pounds of hydrogen peroxide and a corresponding lesser amount of sodium hydroxide or other buffering agents for a ten-fold advantage in chemical cost to give a superior delignification effect. The process is expected to allow fermentation of, or digestion of, 85 to 90% of the sugars, calories, xylose or glucose.

The process utilizes no harsh toxin forming acids and uses a natural combination of chemicals which dissipate under heat and pressures of approximately 280° F. and up to 400 pounds of pressure in less than two minutes. The resulting substrates contain no inhibitors to prevent enzymes or yeast from fermenting the cellulose and hemicellulose to energy for ruminant feed stocks or for use as chemical feed stocks to produce chemicals such as ethanol or acetic acid or butanediol.

Further, the treatment of the substrate under the conditions of the present invention increases, in situ, the normal digestibility of the material to nearly 90% on a dry matter basis.

Further still, the continuous process of the present invention increases product recovery as opposed to a batch process which must be shut down on occasion in order to recover the batch product.

Further still, the process of the present invention requires no presoaking of the raw material for any period longer than the pre-mix time at the front end of the extruder. The temperature range in the extruder is also effective in sterilizing the biomass substrate by killing all bacteria, such as salmonella.

The process of the present invention has several uses. First as a food processing plant, the present invention effectively processes products that are generally discarded, such as hulls, skins, and the pulp of vegetables, grains and fruits, into animal feeds, dietary fibers, absorbent materials, or chemical feed stocks for new industries.

Of major importance, the process of the present invention effectively produces a very light colored dietary fiber from grain hulls or vegetable matter, which can be so customized to alter the soluble portions versus the insoluble. The process of the present invention produces a high percentage dietary fiber in the form of a non-toxic, non-woody, nearly white, fluffy, cellulose material that can be ground to a 120 mesh particle size which is highly water soluble and non-gritty to the taste. Grinding of this fiber can be accomplished with about one-third of the horsepower that is required by the same substrate prior to processing, due to lignin removal. Further, there is considerably less wear on the apparatus.

The dietary fiber produced from the present invention has been found to contain only 24 calories per hundred grams and can be used as an effective replacement or substitute for some of the ingredients in foods such as mashed potatoes, cakes, pasta, cookies, donuts, pancakes, breads, meat loaves, pizza, and gravies. For example, dietary fiber produced by the present invention can be substituted for up to 33% of the white flour in white bread and 40% in cakes and cookies.

Further, the process of the present invention produces a highly absorbent fiber of light manilla color for food additives or pharmaceutical use.

Further still, the process of the present invention advantageously produces a light, fluffy, water absorbent fiber for absorbing body fluids in products such as baby diapers, sanitary napkins, linens and kitty litter.

The process of the present invention also can be utilized to produce a pre-processed compost for greenhouses or mushroom bed material, which allows accelerated growth of any horticulture species, and allows for rapid micelial growth in a sterile environment with all nematodes or bacteria killed during the process. The compost material can be bagged after cooling.

Further still, the process of the present invention can be utilized as a portable waste-processing system used by the fruit or vegetable industry in reducing its disposal costs in many agricultural operations and turning otherwise costly waste products into new sources of fermentable sugar strains for the production of dietary fiber products, chemicals such as acetic acid and ethanol, cattle feeds, and compost material Further objects, features and advantages of the invention will be apparent from the following detailed description when taken in conjunction with the accompanying drawing.

BRIEF DESCRIPTION OF THE DRAWING

The drawing is a schematic plan view of the process of the present invention.

DETAILED DESCRIPTION OF THE INVENTION

The process is directed to a continuous treatment of biomass to produce dietary fiber and other desirable products in a convenient and efficient way. By the use of a pressurized extruder, the non-woody biomass substrate can be conveniently converted into the desirable product in a fast and efficient manner while substantially reducing the amount of necessary chemicals used to delignify the biomass products. For purposes of the present invention, the term "non-woody" is meant to include organic plant material comprising no more than about 20% lignin.

By the term non-woody lignocellulosic substrate or biomass, it is meant that the present invention can treat any non-woody materials including tree fruits, such as apples, apricots, cherries, peaches, pears, and plums; citrus fruits such as lemon, lime, oranges and grapefruits; and bushberries such as blackberries, raspberries, strawberries, and blueberries. Further, cereal grains such as barley, corn, oats, rice, rye, and wheat, as well as the waste material left after the processing of these materials, can be used. In other words, agricultural residues such as corn stalks, wheat straw, prairie grass, hulls of grains and brans, etc., are within the scope of the substrates utilized in the present invention.

Reference is now made to the drawing which illustrates in schematic form the process of the present invention. The biomass substrate, which is preferably chopped or reduced in size to particles not more than one-half inch in length, is fed to a prehydrolysis tank 10 in order to soften and solubilize the biomass. The prehydrolysis tank 10 includes a reaction medium comprising a strong alkali which softens the biomass at a pH between 10.5 and 12.5 and a temperature between 130° and 160° F. Preferably, the prehydrolysis tank 10 is an agitator tank. The preferred alkali in the reaction medium is either sodium hydroxide or potassium hydroxide. In some cases it may be preferred to keep the levels of sodium reduced, especially for food grade applications. Sodium levels may be kept reduced by the use of potassium hydroxide instead of sodium hydroxide. The levels of potassium hydroxide may additionally be reduced by the hydrolyzation of the prehydrolysis tank reaction medium in a subsequent phase and the recycling of a portion of that effluent, containing potassium hydroxide, back to prehydrolysis tank 10. This recycling process may be conducted as many as 7 to 10 times before the buffer loses its effectiveness. The biomass substrate is preferably allowed to remain in the prehydrolysis tank 10 for a period of at least 20 minutes at temperatures between about 130° and 160° F., which time has been shown to be an effective time to produce a sufficiently softened and solubilized biomass for the next step. If desired, the temperature of the reaction medium may be reduced to ambient temperature; however the reaction time will be correspondingly increased.

After the biomass has been sufficiently processed in the prehydrolysis tank 10, the substrate is passed through line 12 and filtered via filter 20. The filter 20 may be any of a number of filters known to the art for removing a reaction medium from a substrate. A preferred filter is a vibrating screen filter. The purpose of the filter 20 is to remove the reaction medium from the prehydrolysis tank 10 for recycling, via line 22, back to the prehydrolysis tank 10. If necessary, the solution which is recycled back to the prehydrolysis tank 10 may be pH corrected by the addition of sodium hydroxide or other buffering material via line 24 from storage container 26. Additionally, it may be necessary to correct the temperature of the recycled solution to be within the preferred 130° to 160° F. temperature prior to entering the prehydrolysis tank 10. The reaction medium may be continuously recycled back to the prehydrolysis tank 10 until the liquid becomes too densely contaminated. The contaminanted reaction medium is then replaced with fresh medium.

After a sufficient amount of the solution from the prehydrolysis tank 10 has been removed by means of the filter 20, the biomass substrate is then transferred via line 28 to a mixer 30. The purpose of the mixer 30 is to remoisten the substrate to a desired moisture percentage, normally 30% to 50% moisture and to add a sufficient amount, preferably between about 2.5% and 4% v/v, of a chelating agent, such as sodium silicate, which will be effective to chelate the metal ions in the solution and coat any metals in the apparatus.

The addition of sodium silicate or other chelating agents is necessary in order to prevent unwanted precipitation of insoluble deposits, such as metals or metal ions. These insoluble deposits may tend to form deposits on any of the downstream components of the apparatus of the present invention. The subsequent peroxide bleaching can then be carried out with fully satisfactory results. The addition of a chelating agent to the substrate also ties up the metal ions in the substrate and water preventing unnecessary oxidation of the hydrogen peroxide by the metal contact. This in turn reduces any premature oxidation of the hydrogen peroxide, reduces the amount of hydrogen peroxide needed by at least 10 to 20% and helps in the bleachig process of the substrate which is very important in producing near white cellulose useful for dietary fibers or absorbancy products. Additionally, the chelating agent coats any knives or discs in the downstream extruder barrel to avoid product burn on or adherence buildup on the surfaces.

The substrate from line 28 is generally processed through the mixer 30 for a time between approximately 2 and 5 minutes at a pressure between approximately 300 to 400 psi and a temperature between 190° and 280° F. If necessary, sodium hydroxide or other alkali chemicals may be added from the buffer solution storage tank 26 via line 32 in order to adjust the pH to between about 11.2 and 12.2. If the hemicellulose is to be retained as in the case of dietary fiber preparation, the pH should be adjusted to between 11.4 and 11.8. The chelating agent is added from the storage tank 34 via line 36. The chelating agent can be added concurrently with the buffering agent prior to leaving the mixer 30.

After a sufficient amount of chelating agent and buffering agent have been added to the substrate, the substrate is then passed via line 38 to the extruder reactor 40. The extruder reactor 40 allows for the effective treatment of the substrate with hydrogen peroxide at higher solids levels. This eliminates a substantial amount of the necessary liquid stream and improves the recovery of carbohydrate products as in the case of animal feeds. The effect of friction and pressure in the extruder is to accelerate the reaction and to reduce the amount of hydrogen peroxide used while maintaining the pH of the substrate at levels between about 11.2 and about 12.2, preferably between 11.4 and 11.8. Ideally, the extruder reactor will process approximately 6,000 lbs. of substrate per hour continuously. The advantage to the use of an extruder reactor is that it replaces steam cooking in a batch process thus making the entire process more efficient.

The extruder reactor is formed of a stainless steel or other noncorrosive material and is modified to cram feed chopped biomass at a 40 to 50% moisture level into a compression chamber with water containing a 4% solution of chelating agent. The solution is pH modified with either the addition of sodium hydroxide, potassium hydroxide, or other buffering agent. The reaction takes place within approximately 1.5 to 5 minutes at a pressure of between approximately 250 and 450 psi, preferably 300 and 400 psi, and a temperature between approximately 150° and 315° F., preferably 190° and 280° F., and most preferably 215° to 275° F. Advantageously, the substrate passing through the extruder 40 may be delignified with as little as 20 to 40 lbs., preferably 25 lbs. of hydrogen peroxide per ton of substrate on a dry matter basis.

Although the extruder reactor may be of twin-screw variety, it is preferably a single screw stainless steel barrel with a steam jacket, capable of food grade operation. The orifice is hydraulically operated to control the temperature and time of the process. Preferred extruders for purposes of the present invention are the Wenger TX-138, X-175, X-185 or X-200 continuous extrusion cookers, which operate at 150–250 horsepower for high capacity industrial applications. These extruders have a feeder device which provides a uniform and controllable feed rate to the extruder.

Pressure gauges are strategically placed to indicate pressure and heat of the substrate throughout the extruder process. As indicated above, the material of the reactor should be stainless steel or a similar corrosion-free material. The reactor may be driven with a variable speed or similar-type speed reduction motor. It will become apparent from the following description of the extruder that the extruder 40 will need several port entries to allow high pressure pumps to introduce water in alkaline form, hydrogen peroxide, sodium silicate or other chelating agent at any point desirable in the process.

The pH of the extruder 40 should be maintained at between 11.2 to 11.8 if hemicellulose is to be retained. If the pH exceeds 11.8, degeneration of the hemicellulose will be enhanced to a point where almost all of the hemicellulose is reduced by hydrolyzation. Therefore, the solubility of the fiber will be reduced. If the hemicellulose retention is desired, the pH must be kept as near to 11.4 as possible. PH monitoring devices will be incorporated into the reactor and subsequent hydrolyzing tanks. Preferably, they will be computerized in order to control the level of operation of the extruder 40.

In operation, the extruder is preferably equipped with a cram feeder to forcefeed the biomass substrate into the throat of the extruder barrel. During the extrusion process, sodium silicate or other chelating agents may be injected, along with buffering agents, oxygen or a suitable gas, and hydrogen peroxide. The biomass enters the extruder 40 as a 35–45% solid substrate.

Oxygen is added to the extruder from an oxygen producing unit 42 via line 44. Oxygen is induced into the extruder in order to help reduce the amount of hydrogen peroxide needed to cause a delignification reaction on the cell walls. Further, the addition of oxygen aids in the initiation and acceleration of the activation of the hydrogen peroxide. A preferred oxygen producing tank is a Prism ® Alpha-Controlled Atmosphere System. The purpose of the Prism ® alpha-system is to generate nitrogen in order to extend the storage life of food products. However, a biproduct of the system is oxygen which is used in the present invention. Of course, other oxygen producing systems may be incorporated into the process of the present invention.

Following the introduction of oxygen, hydrogen peroxide from storage tank 46 is added via line 48. Hydrogen peroxide causes a reaction on the cell walls to allow the hemicellulose and lignin to solubilize and be removed through a subsequent hydrolyzing process. Approximately 20 to 40 lbs. of hydrogen peroxide is all that is necessary to effectively process a ton of substrate through the extruder 40. The hydrogen peroxide is injected approximately $\frac{1}{3}$ of the way into the reactor 40 system following the introduction of oxygen. Hydrogen peroxide is generally diluted to a 10% or less concentration to prevent accidents in transfer. Adequate moisture is needed during this process to prevent too much heat from forming which will cause charring of the material. The induction port 49 for the hydrogen peroxide may be adjusted so that most of the hydrogen peroxide has decomposed by the time the biomass emerges from the reactor 40. The hydrogen peroxide stream preferably passes through a precious metal gauze screen under pressure to immediately initiate the activation of the hydrogen peroxide. Preferred precious metals include platinum and palladium with palladium being most preferred.

It is a substantial benefit of the present invention that the amount of hydrogen peroxide used in the present invention has been reduced from other prior art processes. The reasons for this are several. First, the material is processed in the extruder 40 under elevated temperatures and pressure. Additionally, the material is prevented from contacting surfaces with a sequestering agent, which would cause the premature degeneration of the hydrogen peroxide. Further still, all exposed surfaces of the components of the present invention are of stainless steel or other noncorrosive material.

Advantageously, all hydrogen peroxide is dissipated from the sample collected within 24 hours of the treatment. This is important as levels allowable under FDA will at all times need to be below 3 ppm for GRAS affirmation. Human usage is especially important when it comes to these levels.

The extruder 40 itself may be divided into as many as eight sections, each of which being separated by a steam lock. The first section, or cram feeder is designed to grab and feed the material into the compression zones. This section operates at a speed of 300 RPM with a single screw against a shear block to pressurize. The next section is designed to reabsorb the oxidizing agent, hydrogen peroxide, that has been catalyzed by the metal acetate half way down the reactor. This allows a necessary time for the oxidation process to occur. The final section is an ancular die which extends 2 to 3 inches past the last steam lock.

A preferred extruder reactor includes a single screw stainless steel barrel approximately 5 inches to 16 inches, preferably 5 inches to 5 ½ inches, in diameter and 6 to 8 feet in length. The extruder barrel should be made of a high carbon alloy or stainless steel and having the strength to withstand pressures up to 500 psi and temperatures exceeding 260° F. A typical power source for the extruder is a 200 horsepower, 3-phase electric motor located near the entrance of the extruder. A 6:1 gear reducer reduces the 1800 RPM drive to a 300 RPM extruder speed. A cram feeder hopper powered by a variable speed hydraulic motor feeds the materials, which may have a variable consistency, into the throat of the extruder barrel. A second hopper or mixing pump combines a diluted solution of an alkali agent, such as sodium hydroxide or potassium hydroxide, into the substrate mass in the extruder barrel. Hydrogen peroxide, in diluted form is then injected into the substrate. The developing vapors are withdrawn by exhaust fans. The process material is then augered either to a cooling drum for bagging, to an enzyme or fermentation tank, or to an acid bath for further processing to a dietary or aborband fiber. Remotely located safety sensing devices register both temperature and pressure at the highest point in the extruder barrel. Both manual and automatic shutdown devices are located throughout the system. As a saftey measure, a shroud, generally formed of stainless steel, surrounds the extruder. The shroud includes devices which continuously moniter the toxicity level of the emitted vapors. This safety aspect of the system is able to signal and/or shut down the machine without closing off the vapor exhaustion system until the toxicity level is brought under control.

The biomass leaving the extruder should have a moisture level between approximately 30 and 50% preferable 40% moisture. The temperature of the biomass at this point would generally be in the range of 195° to 200° F. As mentioned previously, all hydrogen peroxide should have been decomposed by the time the biomass leaves the extruder. Additionally, the pH of the biomass at this point will be in the area of 11.5.

Following reaction in the extruder 40, the substrate may be passed via line 50 to cooling drum 52 where the substrate may be cooled and dried. The product 54 may be utilized to feed ruminant livestock, such as cattle and sheep. Alternatively, the product 54 may be converted into a chemical feedstock 58 by the addition of appropriate fungal cellulose enzyme complexes, such as *Trichederma reesei*, which is native to the ruminant's digestive system. The addition of such enzymes converts the cellulose and hemicelluslose to glucose and xylose for the production of ethanol, acetic acid, butanol and other chemical derivatives.

Alternatively, the extrudate from the reactor 40 may be processed through a hydrolyzer 60, i.e., and agitated water tank having a temperature of at least 140° F. The purpose of the hydrolyzer 60 is to wash out hemicellulose.

The product of the hydrolyzer 60 is then transferred via line 62 to a filter 64 which filters out the hydrolyzer solution. The filter 64 acts in a similar fashion to the filter 20, previously described. The product of the filter 64 can then be transferred via line 66 to a conversion tank 68 in order to convert the product to xylose or other chemical feed stocks in a manner similar to that previously described with respect to the cooling drum 52.

Alternatively, the product of filter 64 should be washed at least once and preferably at least two times in an acid bath 70. The purpose of the acid bath is to wash out substantial amounts of the lignin and hemicellulose remaining in the substrate. The pH of the acid bath is reduced to 0.5 to 3 by adding hydrochloric acid from storage tank 72 via line 74. Advantageously, the acid bath acts to further bleach the cellulose fiber in the substrate in order to make the final product brighter and whiter. Following multiple washings in the acid bath 70, the substrate is transferred via line 76 to filter 78 which removes a substantial amount of the acid wash solution. This acid wash solution may be recycled back to acid bath 70 via line 80.

The substrate is then transferred via line 82 to a subsequent washing area 84, having a pH of 6.5 to 7.0. The pH is corrected by the addition of buffering agents, such as calcium carbonate or bicarbonate of soda from storage tank 86 via line 88. This washing process affords a final removal of the bleaching or extraction solutions and solublized compounds therein from the pulp prior to recovery.

Following the pH correction process, the substrate is transferred via line 90 to filter press 92. Filter press 92 is preferably a hydraulic filter press, which reduces the moisture of the substrate to a 55 to 65% moisture level. The liquid which is extracted from the substrate may then be recycled via line 94 back to washer 84 in order to reduce the cost of calcium carbonate and bicarbonate of soda.

The compressed substrate from filter press 92 is then transferred via line 96 to fluffer 100, which acts to break apart the condensed hard packed substrate. The material is then transferred via line 102 to dryer 110, a fluid bed dryer, which dries the fluffed material to a moisture content of approximately 3 to 8%. The temperature in the fluid bed dryer 110 should not exceed 180° F. in order to obtain the best coloring for the fiber substrate.

Following drying, the substrate is passed via line 112 to a cutting mill 120, which grounds the substrate fiber through preferably a 60 mesh screen with a cutting mill. Although other cutters, such as hammer or ball mill types may be used, cutting mills are preferred. This is because hammer and ball mills tend to compress the fluffy cellulose and diminish the puffing or absorbing qualities of the fiber.

The final product leaving the cutting mill 120 via line 122 enters a powder tank 130 in preparation to be bagged at 132.

The entire system of the present invention may be hydraulically controlled to maintain certain pressures, temperatures and retention times, depending upon the substrate used, the amount of water used and the amount of delignification desired. The whole system can of course be computerized and controlled by pressures, heat or end results and the capacity desired. The apparatus may be powered by diesel power with water circulation through the diesel engine block used as a boiler, along with the function which would provide heat for cooking in the extruder. Excess hot water would then be recycled to the water jacketed pre-pulper tank and then back to the diesel motor block. Diesel would power the extruder and hydraulic systems to control the orifice on the extruder.

The final product of the present invention preferably has a particle size small enough to pass through a 100 mesh screen. Such a particle is acceptable as a food grade material for total dietary fiber. Additionally, this fiber has a brightness reading of over 80 GE units as measured by a General Electric brightness meter. The dietary fiber is also a food product acceptable to the FDA residue requirements.

Thus, the need for a nearly white, high percentage dietary fiber can be met by applying the process of the present invention which simultaneously delignifies, bleaches, shears, sterilizes and liquifies the substrate causing both the lignin and hemicellulose to be removed, leaving 80% or more cellulose in the final product. The final product is a non-toxic, non-woody white fluffy cellulose material which can be ground to a 120 mesh particle size and which is highly soluble and non-gritty to the taste.

It is within the scope of the present invention to customize the apparatus to leave in more lignin and hemicellulose or take out more by simply changing the pH level during the process. Additionally, the process may be mobilized as a portable unit, which would effect tremendous savings on the cost of transorting the substrate for livestock feeding.

The following examples are given to illustrate certain preferred embodiments of the process of the present invention.

EXAMPLE 1

Example 1 is designed to illustrate the delignification of a non-woody lignocellulose biomass substrate to a feed suitable for ruminant digestion. The biomass substrate is chopped to a size not exceeding ½ inch and forwarded to a prehydraulysis tank containing water as a reaction medium. Potassium hydroxide is added to the water to raise the pH to 11.5. The temperature of the water is approximately 130° F. The substrate is allowed to react in this mixture for approximately 20 minutes. The substrate is then pumped through a filter extractor to remove the lignin. The reaction fluid is then recycled back to the prehydraulysis tank and the substrate is conveyed to a mixer where the pH is converted to 11.5 and a chelating agent is added at a 2.5 to 4% v/v level. The substrate is processed through the mixer for approximately 2 ½ minutes at a pressure between approximately 300 and 400 psi and a temperature of about 190°.

The substrate is then fed to an extruder reactor, and oxygen is then introduced to create an oxygen atmosphere. Subsequently, a 10% solution of hydrogen peroxide is introduced through a high pressure orifice through a palladium gauze and into the reactor. The hydrogen peroxide is added at a rate of 25 lbs. of hydrogen peroxide per ton of substrate on a dry matter basis. After reacting for approximately 45 to 60 seconds, the substrate emerges through a hydraulically controlled valve in the extruder reactor. At this point, the temperature of the substrate environment is between approximately 200 to 265° F.

The substrate is then conveyed to a cooling drum where the substrate is cooled and dried. The product of the cooling drum may then be utilized to feed ruminant feed stock. Alternatively, the product can be converted into a chemical feed stock by the subsequent addition of appropriate enzymes.

EXAMPLE 2

Example 2 illustrates a preferred process for producing a dietary fiber. The process according to Example 1 is followed through the extruder reactor. Rather than forwarding the substrate to a cooling drum, the substrate is hydrolyzed in an agitated vat in a pH approximately 11.4 to 11.8 for approximately 30 minutes. The substrate is then passed through a vibrating filter to separate the substrate from the reaction fluid. The fluid may then be pumped back to a recycle silo to concentrate the sugars and hemicellulose. The substrate is then washed through an acid bath at a pH of 1.5. After the acid bath, the acid is washed off and the pH of the substrate is converted to at least 6.0. The acid bath may be recycled back to the supply tank for further use. The product is then hydraulically pressed to decrease the total moisture content to the low 70%, followed by fluffing and drying in a fluid vat dryer to bring the moisture to no more than 8%, preferably 4%. The product is then forwarded to a cutting mill to cut the fibers to a 70 to 120 mesh size. The prepared dietary fiber may then be bagged for transport.

EXAMPLE 3

Example 3 illustrates the process for the production of an absorbant fiber for industrial purposes. The process of Example 2 is followed with the exception that the substrate leaving the extruder reactor is hydrolyzed in an agitated vat having a pH between 11.8 and 12.2. At this pH, most of the hemicellulose is removed and only the cellulose remains in the substrate.

It is understood that the invention is not confined to the particular construction and arrangement of parts herein illustrated and described, but embraces such modified forms thereof as come within the scope of the following claims.

What is claimed is:

1. A process for continuously treating a non-woody lignocellulosic substrate consisting of organic plant material having no more than about 20% lignin content, the process consisting essentially of:
   (a) reacting the substrate in a reaction medium including an aqueous solution of a strong alkali at a pH in the range of about 10.5 and 12.5;

(b) reacting a chelating agent with the substrate the chelating agent being in an amount and for a time effective to chelate any metal ions in the solution;

(c) continuously feeding the product of step b) to an aqueous solution in a pressurized extruder reactor and reacting the substrate in an oxygen atmosphere at a temperature between about 150° and 315° F. and a pressure between about 250 and 450 psi, and in the presence of hydrogen peroxide for a period of time effective to delignify the substrate wherein the hydrogen peroxide is added to the extruder at a rate of between about 20 and 40 pounds of hydrogen peroxide per ton of substrate.

2. The process of claim 1 wherein the substrate is selected from the group comprising tree fruits, citrus fruits, bushberries, cereal grains and agricultural residues.

3. The process of claim 1 wherein the substrate is reduced in size to a particle not more than one-half inch in length prior to reacting in the reaction medium.

4. The process of claim 1 wherein the substrate is reacted in a reaction medium in a prehydrolysis tank, wherein the substrate is softened in the reaction medium at a temperature between 130° and 160° F.

5. The process of claim 4 wherein the prehydrolysis tank is an agitator tank.

6. The process of claim 1 wherein the alkali is selected from the group consisting of sodium hydroxide and potassium hydroxide.

7. The process of claim 1 wherein the alkali is potassium hydroxide.

8. The process of claim 1 wherein the substrate is reacted in the reaction medium of step (a) for a period of at least 20 minutes.

9. The process according to claim 1 wherein the reaction medium is removed from the substrate prior to feeding the substrate to a pressurized extruder reactor.

10. The process of claim 9 wherein the reaction medium is filtered from the substrate.

11. The process of claim 10 wherein the filtered reaction medium is recycled back to the reaction medium including an aqueous solution of a strong alkali at a pH in the range of about 10.5 to 12.5.

12. The process of claim 1 wherein the chelating agent is added in an amount between about 2.5% and 4.0% v/v.

13. The process of claim 12 wherein the chelating agent is sodium silicate.

14. The process of claim 1 wherein the chelating agent is added in an amount sufficient to reduce the amount of hydrogen peroxide necessary by approximately 10 to 20%.

15. The process of claim 1 wherein the chelating agent is reacted with the substrate for a time between approximately 2 and 5 minutes and at a pressure between approximately 300 and 400 psi, a temperature between 190° and 280° F. and a pH of approximately 11.4.

16. The process of claim 1 wherein the extruder reactor is formed of a noncorrosive material and is modified to cram feed the substrate at a 40 to 50% moisture level.

17. The process of claim 1 wherein the substrate is reacted in the extruder reactor at a pH between about 11.2 and about 11.8.

18. The process of claim 1 wherein the substrate is reacted in the extruder reactor at a pH of about 11.5.

19. The process of claim 1 further consisting essentially of adding chelating agents and buffering agents to the aqueous solution of the extruder reactor.

20. The process of claim 1 further consisting essentially of washing the substrate in an aqueous wash solution to remove the hemicellulose from the substrate.

21. The process of claim 20 wherein the substrate is washed in an agitated water tank at a temperature of at least 140° F.

22. The process of claim 20 further consisting essentially removing the aqueous wash solution.

23. The process of claim 20 further consisting essentially of washing the substrate in an acid bath including an aqueous acid bath solution having a pH between about 0.5 and 3.0, followed by washing the substrate in an aqueous pH correction solution, where a buffering agent is added to the aqueous pH correction solution to adjust the pH to between about 6.5 and 7.0.

24. The process of claim 23 wherein the acid in the acid bath solution is hydrochloric acid and the buffering agent in the pH correction solution is selected from the group consisting of calcium chloride and bicarbonate of soda.

25. The process of claim 23 further consisting essentially of subsequently reducing the moisture content of the substrate.

26. The process of claim 23 further consisting essentially of the following steps in sequence:
(d) subsequently reducing the moisture content of the substrate to a moisture level between about 55 and 65%;
(e) fluffing the substrate; and
(f) drying the substrate at a temperature no greater than about 180? F.

27. A process for continuously preparing a nearly white, non-woody, delignified dietary fiber suitable for food grade consumption, wherein the fiber contains at leat 80% cellulose, the process consisting essentially of the following steps of sequence:
(a) reacting an organic non-woody lignocellulosic substrate having no more than about 20% lignin in a reaction medium including an aqueous solution of a strong alkali at a pH in the range of about 10.5 and 11.8;
(b) reacting a chelating agent with the substrate, the chelating agent being in an amount and for a time effective to chelate any metal ions in the solution;
(c) continuously feeding the substrate of step (b) to a pressurized extruder reactor and reacting the substrate in an oxygen atmosphere at a temperature between about 150° and 315° F. and at a pressure between about 250 and 450 psi, and in the presence of hydrogen peroxide for a period of time effective to delignify the substrate wherein the hydrogen peroxide is added to the extruder at a rate of between about 20 and 40 lbs. of hydrogen peroxide per ton of substrate;
(d) washing the substrate in an aqueous wash solution to remove the hemicellulose and lignin from the substrate;
(e) washing the substrate in an acid bath including an aqueous acid bath solution having a pH between about 0.5 and 3.0;
(f) washing the substrate in an aqueous pH correction solution, wherein a buffering agent is added to the aqueous pH correction solution to adjust the pH to between about 6.5 and 7.0;

(g) reducing the moisture content of the substrate to a moisture level between about 55% and 65%;

(h) fluffing the substrate; and (i) drying the substrate at a temperature no greater than about 180° F.

28. The process of claim 27 wherein the substrate is selected from the group comprising tree fruits, vegetables, citrus fruits, bushberries, cereal grains and agricultural residues.

29. The process of claim 27 wherein the substrate is reacted in a reaction medium in a prehydrolysis tank, wherein the substrate is softened in the reaction medium at a temperature between 130° and 160° F.

30. The process of claim 27 wherein the chelating agent is added in an amount between about 2.5% and 4.0% v/v.

31. The process of claim 27 wherein the chelating agent is reacted with the substrate for a time between approximately 2 and 5 minutes and at a pressure between approximately 300 and 400 psi, a temperature between 190° and 280° F. and a pH of approximately 11.4.

32. The process of claim 27 further consisting essentially of removing the hemicellulose and lignin from the substrate in an agitated water tank at a temperature of at least 140° F.

33. A process for continuously preparing a ruminant feed source consisting essentially of the following steps in sequence:

(a) reacting a non-woody lignocellulosic substrate consisting of organic plant material having no more than 20% lignin in a reaction medium including an aqueous solution of a strong alkali at a pH in the range of about 10.5 and 12.5;

(b) reacting a chelating agent with the substrate, the chelating agent being in an amount effective to chelate any metal ions in the solution;

(c) continuously feeding the substrate of step b) to a pressurized extruder reactor and reacting the substrate in an oxygen atmosphere at a temperature between about 150° and 315° F. and at a pressure between about 250 and 450 psi, and in the presence of hydrogen peroxide for a period of time effective to delignify the substrate wherein the hydrogen peroxide is added to the extruder at a rate of between about 20 and 40 lbs.of hydrogen peroxide per ton of substrate; and (d) cooling the substrate.

34. A process for continuously preparing a highly absorbant fiber source consisting essentially of the following steps in sequence:

(a) reacting a non-woody lignocellulosic substrate consisting of organic plant material having no more than about 20% lignin content in a reaction medium includng an aqueous solution of a strong alkali at a pH in the range of about 10.5 and 12.5;

(b) reacting a chelating agent with the substrate, the chelating agent being in an amount and for a time effective to chelate any metal ions in the solution;

(c) contnnuously feeding the substrate of step b) to a pressurized extruder reactor in an oxygen atmosphere at a temperature between about 150° and 315° F. and at a pressure between about 250 and 450 psi, and in the presence of hydrogen peroxide for a period of time effective to delignify the substrate wherein the hydrogen peroxide is added to the extruder at a rate of between about 20 and 40 lbs. of hydrogen peroxide per ton of substrate;

(d) washing the substrate in an aqueous wash solution to remove the hemicellulose and lignin from the substrate;

(e) washing the substrate in an acid bath including an aqueous acid bath solution having a pH between about 0.5 and 3.0;

(f) washing the substrate in an aqueous pH correction solution, wherein a buffering agent is added to the aqueous pH correction solution to adjust the pH to between about 6.5 and 7.0;

(g) reducing the moisture content of the substrate to a moisture level between about 55% and 65%;

(h) fluffing the substrate; and (i) drying the substrate at a temperature no greater than about 180° F.

* * * * *

UNITED STATES PATENT AND TRADEMARK OFFICE
CERTIFICATE OF CORRECTION

PATENT NO. : 4,842,877

DATED : June 27, 1989

INVENTOR(S) : George J. Tyson

It is certified that error appears in the above-identified patent and that said Letters Patent is hereby corrected as shown below:

Column 9, line 52, delete "absorband" and insert --absorbant--.

Column 9, line 64, after "50%", insert --,--.

Column 10, line 12, delete "hemicelluslose" and insert --hemicellulose--.

Column 13, line 15, delete "fromthe" and insert --from the--.

Column 14, line 11, before "removing", insert --of--.

Column 14, line 34, delete "180?" and insert --180°--.

Column 14, line 39, delete "leat" and insert --least--.

Column 15, line 36, between "amount" and "effective", insert --and for a time--.

Column 16, line 18, delete "contnnuously" and insert --continuously--;

UNITED STATES PATENT AND TRADEMARK OFFICE
CERTIFICATE OF CORRECTION

PATENT NO. : 4,842,877
DATED : June 27, 1989
INVENTOR(S) : George J. Tyson

It is certified that error appears in the above-identified patent and that said Letters Patent is hereby corrected as shown below:

Column 16, line 17, between "reactor" and "in", insert --and reacting the substrate--.

Signed and Sealed this

Fifth Day of June, 1990

Attest:

HARRY F. MANBECK, JR.

*Attesting Officer*　　　　*Commissioner of Patents and Trademarks*